United States Patent [19]

Mehra

[11] Patent Number: 5,129,394
[45] Date of Patent: Jul. 14, 1992

[54] METHOD AND APPARATUS FOR CONTROLLING HEART RATE IN PROPORTION TO LEFT VENTRICULAR PRESSURE

[75] Inventor: Rahul Mehra, Stillwater, Minn.

[73] Assignee: Medtronic, Inc., Minneapolis, Minn.

[21] Appl. No.: 638,286

[22] Filed: Jan. 7, 1991

[51] Int. Cl.$^5$ ............................................. A61N 1/362
[52] U.S. Cl. .......................... 128/419 PG; 128/419 D
[58] Field of Search .................... 128/419 PG, 419 D

[56] References Cited

U.S. PATENT DOCUMENTS

| Re. 27,757 | 3/1987 | Mirowski | 128/419 D |
|---|---|---|---|
| 3,358,690 | 12/1967 | Cohen | 128/419 PG |
| 3,857,399 | 12/1974 | Zacouto | 128/419 P |
| 4,407,296 | 10/1983 | Anderson | 128/675 |
| 4,485,813 | 12/1984 | Anderson et al. | 128/675 |
| 4,566,456 | 1/1986 | Koning et al. | 128/419 PG |
| 4,774,950 | 10/1988 | Cohen | 128/419 D |
| 4,899,751 | 2/1990 | Cohen | 128/419 PG |
| 4,899,752 | 2/1990 | Cohen | 128/419 PG |

FOREIGN PATENT DOCUMENTS

8701947  4/1987  PCT Int'l Appl.

OTHER PUBLICATIONS

"Development of Implanted Cardiac Pacemakers", L. Juhasz, Digest of 6th Intl. Conf. on Medical Electronics and Biological Engineering, 1965, Tokyo, pp. 85-86.
"Ventricular Fibrillation Detection by Intramyocardial Pressure Gradients", 1983, Denys et al., in Proceedings of the 7th World Symposium on Cardiac Pacing, pp. 821-826.
"Automatic Defibrillator, Antitachy Pacemaker and Cardioverter", Computers and Cardiology, pp. 45-48, 1986, IEEE Computer Society Press.
"Design for an Implantable Defibrillator Using a Novel Heart Beat Sensor", Japanese Journal of Medical and Biological Engineering, 1984, pp. 43-48, by Makino.
"Automatic Detection of Ventricular Fibrillation with Chronically Implanted Pressure Sensors", by Walter Olson et al. (abstract), JACC, vol. 7, No. 2, Feb., 1986, p. 182A.

Primary Examiner—William E. Kamm
Assistant Examiner—Scott M. Getzow
Attorney, Agent, or Firm—Reed A. Duthler; Harold R. Patton

[57] ABSTRACT

A method and apparatus for sensing in vivo blood pressure proportional to the left ventricular pressure for detecting ventricular tachyarrhythmias or the cardiovascular status in congestive heart failure, and/or for adjusting the rate of a pacemaker. A lead with a pressure sensor near its distal end is placed transvenously through the coronary sinus and located in the coronary vein. When in place, a bulge or an inflatable balloon proximal to the pressure sensor may be used to acutely occlude the coronary vein until the sensor fibroses in. The balloon may be reinflated prior to pressure measurements. The pressure that is sensed in that location is proportional to the left ventricular pressure. Values representing the left ventricular pulse, systolic and diastolic pressures, as well as the differentiated rate of change (i.e., dP/dt), gross rate of change ($\Delta P/\Delta t$) and mean or average of such pressure values are all or selectively developed by software algorithms and implemented in microprocessor based control circuitry. In one preferred embodiment, one or more of the values are utilized in software implemented algorithms to cause a pacemaker to pace the heart at a required rate to achieve a desired cardiac output. Alternatively, these left ventricular pressure related values may be employed to confirm the absence of mechanical pumping action of the heart which, in conjunction with other cardiac signals, confirm the existence of a tachyarrhythmia requiring anti-tachy pacing, cardioversion or defibrillation.

40 Claims, 3 Drawing Sheets

METHOD AND APPARATUS FOR CONTROLLING HEART RATE IN PROPORTION TO LEFT VENTRICULAR PRESSURE

BACKGROUND OF THE INVENTION

1. Field of the Invention

The present invention relates to a method and apparatus for deriving pressure signals relative to the blood pressure within the left ventricle of a patient's heart and employing those signals to control pacing rate of a pacemaker in response to the physiologic needs of the cardiovascular system and/or to confirm the existence of a pathologic tachyarrhythmia and trigger the delivery of an appropriate therapy, such as anti-tachyarrhythmia pacing, cardioversion or defibrillation.

2. Description of the Prior Art

Advances in the treatments of bradyarrhythmias (slow heart beat) and tachyarrhythmias (fast heart beat) with implanted devices capable of detecting each condition and providing the appropriate therapy resulted in numerous advances in the art since simple fixed rate pacemaker were first implanted about thirty years ago. The control of the heart's rhythm by monitoring both electrical and mechanical heart function has been a goal of researchers in the field over that same period of time. For example, the 1961 pamphlet by Dr. Fred Zacouto, Paris, France, "Traitement D'Urgence des Differents Types de Syncopes Cardiaques du Syndrome de Morgangni-Adams-Stokes", (National Library of Medicine), describes an automatic pacemaker and defibrillator responsive to the presence or absence of the patient's blood pressure in conjunction with the rate of the patient's electrocardiogram. Very generally, a simple algorithm employing the patient's heart rate as evidenced by the electrical R-waves and the patient's blood pressure pulse was employed to: (1) operate a pacemaker pulse generator at a fixed rate in the presence of both signals recurring at less than a minimum rate or escape interval; (2) trigger the delivery of a defibrillation shock to the heart in the presence of a heart rate exceeding a tachyarrhythmia detect upper rate threshold in conjunction with the absence of a blood pressure signal over a variable period (such as thirty seconds); and, (3) inhibit both the pacemaker and defibrillator in the presence of both R-waves and blood pressure pulses recurring at a frequency exceeding the lower rate threshold but falling below the tachyarrhythmia detect threshold. It was long recognized earlier in medicine that the patient's blood pressure and electrocardiogram constituted the two most familiar and direct diagnostic tools for assessing the condition of the patient's cardiovascular system.

In this regard, it was also recognized early in the history of cardiac pacing that the patient dependent upon fixed rate pacing stimulation suffered cardiovascular insufficiency as his heart was able to increase its output (cardiac output) by only a limited amount in response to physiologic need. In normal hearts, the cardiovascular system responds to physiologic need by increasing both the heartbeat rate and its volume and systolic pressure (thereby increasing stroke volume and cardiac output) in response to physiologic need and as the heartbeat rate is limited in the pacing dependent patient to the fixed pacer rate, the heart's blood pressure and volume could increase proportional to physiologic need only to a limited extent. Thus, it was suggested by Juhasz in his 1965 article "Development of Implanted Cardiac Pacemakers", Digest of 6th *Int'l Conf. on Medical Electronics and Biological Engineering,* 1965, Tokyo, pp. 85-86, that blood pressure, among other parameters of the cardiovascular system, could be used as a forward transfer control value to vary pacing rates as a function of the blood pressure value, thus releasing the heart from the constraint imposed by the fixed base or lower pacing rate and allowing it to beat up to the pulse generator's upper pacing rate limit.

These early researchers were followed by numerous examples of the use of pressure signals of one form or another to control pacing rate or verify the presence of a tachyarrhythmia and trigger the delivery of appropriate therapies. For example, it has been proposed to sense pressure in the right atrium and to utilize a signal derived therefrom to affect and control right ventricular pacing as disclosed in Cohen U.S. Pat. No. 3,358,690. In addition, the Zacouto U.S. Pat. No. 3,857,399 (FIG. 19) discloses a pressure sensor on an extension of a pacing lead adapted to be forced into or through the ventricular septum to measure the intramyocardial pressure within the septum, and/or the actual left ventricular pressure. The signal derived from one or both of these sensors represents an average or mean pressure that varies over relatively long periods of time in a manner similar to that described in the Kresh PCT Publication No. WO87/01947. More recently, the publication of Todd J. Cohen, entitled "A Theoretical Right Atrial Pressure Feedback Heart Rate Control System to Restore Physiologic Control to a Rate Limited Heart", PACE, Vol. 7, pp. 671-677, July-August, 1984, discloses a system for comparing the mean right atrial pressure signal with a baseline signal and developing an error signal which, after processing, is used to control the pacing rate.

In addition, the microprocessor based implantable pacemaker and ventricular pressure sensing lead disclosed in Koning et al, U.S. Pat. No. 4,566,456, relates right ventricular systolic pressure, the gross rate of change over time of the pressure ($\Delta P/\Delta t$) and/or the time derivative ($dP/dt$) of the systolic pressure with the rate needed to produce the desired cardiac output. Koning, in one algorithm, detects the right ventricular systolic pressure peak valves, averages N peak values and compares the current average to the preceding stored average value to detect the change in average pressure over time ($\Delta P/\Delta t$). That signal is employed to "look up" a $\Delta R$ or pacing rate change used to modify the pacing rate R.

More recently, Cohen U.S. Pat. No. 4,899,751 discloses a pacing system relying on a pressure signal from a pressure sensor located in the cardiovascular system, including the four chambers of the heart, coupled with signal processing circuitry for developing short term and long term mean (or average) pressure related control signals therefrom. The escape interval or rate of the pacemaker is controlled as a function of the difference between the short term and long term mean pressure values. Cohen, U.S. Pat. No. 4,899,752, provides a somewhat different algorithm in that the current mean pressure values are compared against fixed threshold values and the difference is employed to modify the pacing rate.

Medtronic U.S. Pat. Nos. 4,407,296, 4,432,372 and 4,485,813 describe various transvenous pressure sensors with associated pacing electrodes adapted to be positioned in a heart chamber to develop pressure values to control the operation of rate responsive pacemakers or to detect pathologic tachyarrhythmias and trigger the delivery of appropriate therapies.

In regard to the use of a blood pressure related signal detected within a heart chamber to confirm the detection of a tachyarrhythmia and trigger the delivery of an appropriate therapy, the initial system proposed by Mirowski et al in U.S. Pat. No. Re 27,757 relied upon the decrease in the amplitude of a pulsatile (systolic) right ventricular pressure signal below a threshold over a predetermined period of time ($\Delta P/\Delta t$) to commence the charging of a high energy output capacitor and deliver a shock to the heart if the pressure signal did not increase above the threshold during the charging time. The short lived pressure sensor available to Mirowski at that time was abandoned in favor of electrocardiogram rate and morphology detection.

More recently, the use of intramyocardial pressure and left ventricular pressure has been explored by a research group from Belgium (see, for example, the paper by Denys et al entitled "Ventricular Defibrillation Detection by Intramyocardial Pressure Gradients" in PROCEEDINGS OF THE SEVENTH WORLD SYMPOSIUM ON CARDIAC PACING, pp. 821–826, Verlag, 1983, and subsequent papers, such as "Automatic Defibrillator, Antitachy Pacemaker and Cardioverter", COMPUTERS AND CARDIOLOGY, IEEE COMPUTER SOCIETY PRESS, pp. 45–48, Oct. 7–10, 1986, and other papers by this group. This group has advocated the use of left ventricular impedance or pressure or a left ventricular pressure related signal over right ventricular pressure, and they resorted to use of ventricular intramyocardial pressure because of the difficulty of directly measuring pressure in the left ventricle and atrium.

In addition, a Japanese group has published papers such as "Design for an Implantable Defibrillator Using a Novel Heartbeat Sensor", *Japanese Journal of Medical and Biological Engineering,* 1984, pp. 43–48, by Makino et al. The Japanese group's sensor detects the pressure in the right ventricle using a catheter born electrode, or microphone, heartbeat sensor. The absence of a heartbeat for 3.5 seconds causes the fibrillation detector to switch the high voltage converter into operation.

The comparison of a current average pressure value to a longer term average control value derived from the heart during normal sinus rhythm to detect ventricular arrhythmias and trigger cardioversion/defibrillation therapies in response to a significant decrease in the current value was proposed by Olson et al, in "Automatic Detection of Ventricular Fibrillation with Chronic Pressure Sensors", (abstract), JACC, Vol. 7, No. 2, Feb., 1986, p. 182A.

More recently Cohen, U.S. Pat. No. 4,774,950, describes a system employing mean pressure values from any of the four chambers of the heart representative of the long-term mean base line pressure and the short-term current mean pressure to indicate or confirm the indication of a tachyrhthmia and to trigger cardioversion/defibrillation shock therapies when the difference between the two mean pressure values exceeds a predetermined threshold value.

The truest indication of the degree of hemodynamic compromise of the malfunctioning heart is the left ventricular pressure which is measurable only with some difficulty. For example, Zacouto, Kresh, the Belgian group and Cohen (in the '751 and '950 patents) all have sought in one way or another to determine the left ventricular pressure by locating a pressure sensor within the left ventricle or within the myocardial tissue. Placing and retaining a pressure sensor in either location involves some risk that the high pressure, left ventricular chamber will be breached at the point of penetration causing the patient to hemorrhage as expressly commented on by the Belgian group. Thus with current technology, it is undesirable to so situate a pressure sensing transducer. However, the desirability of measuring is directly as possible the left atrial o ventricular blood pressure remains high.

SUMMARY OF THE INVENTION

According to the invention, there is provided an implantable apparatus for developing various pressure values proportional to the left ventricular pulse, systolic, and diastolic pressures, as well as the differentiated rate of change (dP/dt), gross rate of change ($\Delta P/\Delta t$) and mean or average of such pressure values by indirectly measuring without invading the left chambers or the myocardium in order to determine the adequacy of the pumping action of the heart and control the operation of a rate responsive bradycardia treating pacemaker and/or the operation of a system for pacing, cardioverting and/or defibrillating to correct tachyarrhythmias.

According to the present invention, there is provided a method and apparatus for controlling cardiac tachyarrhythmias by passing an electrical current through the heart which comprises disposing at least first and second electrodes in relation to the heart, disposing a pressure transducer within the coronary sinus or a coronary vein adjacent to the left heart chambers, detecting a signal proportional to the left heart chamber blood pressure signals by said pressure transducer and providing a first signal in response to normal heart pumping and a second signal in response to abnormal heart pumping characteristic of hemodynamic insufficiency, and supplying cardioversion or defibrillation energy to said heart in response to said second signal by application of stimulating pulses across said electrode.

More specifically, the first and second signals may be related to one or more of the aforementioned pressure values. In addition, the first and second signals may be derived by comparing the current pressure signals (or values) to a fixed baseline pressure signal (or value) or to a baseline pressure signal (or value) derived from a series of normal pressure signals (or values) detected (or derived) from the pressure sensor.

According to the present invention, there is provided a further method and apparatus for providing electrical energy to the heart to maintain and/or restore cardiac output at a value meeting the patient's physiologic or metabolic requirements, wherein the method and apparatus is realized by: implanting a pulse generator and control circuitry which may be realized by a software driven microprocessor within the patient's body; coupling a lead system to the pulse generator to situate an electrogram sensing and stimulating electrode in or adjacent to the ventricle and a pressure sensor within the coronary sinus or deep cardiac vein; periodically measuring the pressure within the vessel in order to develop a pressure related signal of any of the aforementioned pressure values representative of the left ventricular pressure; processing the signal representative of the left ventricular pressure in order to develop a control signal for operating the pulse generator to restore or regulate cardiac output.

More particularly, the method and the apparatus of the present invention may be implemented with a electrogram sensing or pacing electrode and/or a cardioversion/defibrillation electrode on the body of the lead bearing the pressure sensor adapted to be disposed in the coronary sinus or coronary vein. A mechanism for blocking the great cardiac vein until the pressure sensor is securely fibrosed into the vessel may be provided and take the form of a radially disposed collar or expandable balloon member located proximally to the pressure sensor and adapted to be expanded at implant or prior to pressure measurement.

Pressure measurements may be made on a continuing basis, with pressure measurements initiated in response to sensed or paced ventricular contractions. Alternatively, if the pressure measurement is to be used only for detection of tachyarrhythmias, or discrimination of tachyarrhythmias from high sinus rates, pressure measurements may be initiated in response to the detection of high heart rates. Alternatively, pressure measurements may be taken intermittently, under control of a real time clock within the pulse generator.

The signal processing algorithm may provide for measuring and storing baseline pressure values for subsequent comparison to current pressure values and providing a pacing rate control or cardioversion/defibrillation therapy triggering signal in response to the difference between the two signals. In this regard, the electrogram or R-wave rate may be employed to place bounds on the function of the system in treating brady and tachyarrhythmias.

From a somewhat different point of view, the invention can be seen as a method and apparatus for treating a malfunctioning heart by providing electrical pulse energy to the heart to restore or maintain cardiac output in response to at least one hemodynamic pressure value related to the pressure values in the left chambers of the heart, measured by means of a pressure sensor located within the coronary sinus, great cardiac vein, or other coronary vein. Changes of pressure values are employed to vary the frequency of pacing energy pulses within upper and lower rate limits, whereas diminished or nonexistent pressure values are employed to trigger the delivery of cardioversion/defibrillation energy stimulation pulses. The method and apparatus may be implemented in a microprocessor based dual chamber rate responsive pacemaker and tachyrhythmia control system.

More specifically, the present invention contemplates a method and apparatus for regulating cardiac pacing rate in response to a patient's left heart blood pressure which comprises: disposing at least first and second electrodes in relation to the heart; disposing a pressure transducer within the coronary sinus region of the heart adjacent to the left heart chambers; detecting pressure by said pressure transducer and providing a pressure signal related thereto; developing a current blood pressure value from a series of current pressure signals; providing a baseline blood pressure value; comparing the current blood pressure value to the baseline blood pressure value and developing a difference value; deriving a rate control signal from said difference value; and supplying pacing energy stimulation pulses to said electrodes at a rate established by said rate control signal. The method and apparatus for providing a baseline blood pressure value may further comprise developing said baseline blood pressure value from a baseline series of blood pressure signals greater in number than said series of current blood pressure signals. Alternatively, the baseline blood pressure may be a fixed value. This method and apparatus may employ any of the aforementioned pressure values.

BRIEF DESCRIPTION OF THE DRAWINGS

The above and still further objects, features and advantages of the present invention will become apparent from the following detailed description of the presently preferred embodiments, taken in conjunction with the accompanying drawings, and, in which.

DETAILED DESCRIPTION OF THE PREFERRED EMBODIMENT

In the following description of the preferred embodiments of the present invention, it will be understood that the illustrated embodiments encompass both the detection and treatment of brady and tachyarrhythmias, whereas the invention may be used advantageously in either system alone. Consequently, although the drawings illustrate the advantageous uses of the invention in combination, it will be understood the detection of the left chamber pressure by way of a pressure transducer situated a coronary vein may be employed advantageously as stated hereinbefore, in a first system for controlling the pacing rate of a bradycardia pacing pulse generator, or the detection of cardiac insufficiency in order to detect or confirm the detection of a hemodynamically compromising tachyarrhythmia and to trigger the appropriate therapy or in a third system embodying all of the features of both the bradycardia and tachyarrhythmia detection and treatment systems.

Figure 1:
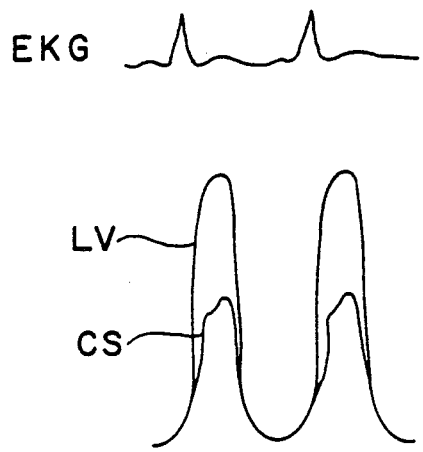
FIG. 1 illustrates the correlation between the electrocardiogram and the corresponding pressure wave forms taken the left ventricular cavity (LV) and from the coronary sinus (CS).

FIG. 1 shows a simulated EKG tracing, with illustrative wave forms illustrating the corresponding pressure waves as measured in the left ventricle (LV) and the occluded coronary sinus or cardiac vein (CS). As can be seen by these tracings, the pressure in an occluded coronary vein is proportional to the pressure in the left ventricle. Measurements of the pressure in the coronary vein thus provide a workable substitute for direct measurement of pressure within the left ventricular cavity.

Figure 2:
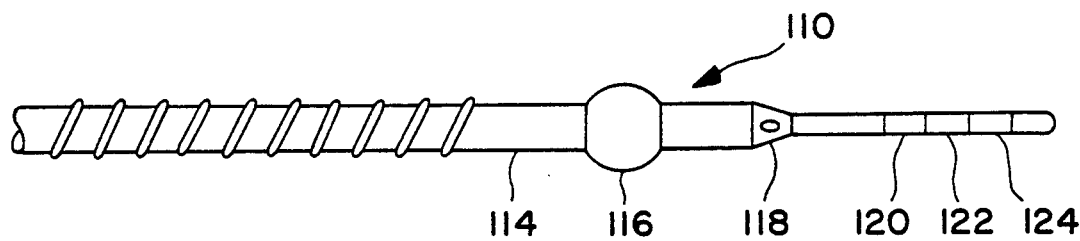
FIG. 2 is a partial plan view of a first embodiment of the pressure transducer bearing coronary sinus pacing and/or cardioversion lead of the present invention.

Turning then to FIG. 2, the distal portion of the pacing/cardioversion/pressure sensing lead of the present invention is depicted in a first embodiment. In FIG. 2, the distal portion 110 includes an elongated relatively high surface area cardioversion coil electrode 112 wrapped about the outer insulation 114 proximal to the solid spherical occluding member 116. The pressure transducer 118 and optional first and second pacing/sensing electrodes 120 and 122 are located distally from the occluding member 116. Alternately, atrial pacing and/or sensing electrodes may be placed proximal to the coil electrode 112 such that they are located adjacent the opening of the coronary sinus into the right atrium, when the lead is implanted. Pacing and sensing electrodes may be omitted and may be dispensed with entirety, if separate atrial or ventricular pacing and/or sensing electrodes are provided on other leads. The distal end 124 of the lead is fabricated of tapered insulating material which is flexible in order to guide the depicted distal portion of the lead into the coronary sinus and then into a coronary vein.

The bipolar pacing/sensing electrodes 120 and 122 in the lead of FIG. 1 are coupled through conductors within the lead body to pacing/sensing circuitry within a pulse generator to detect the near field EGM and provide a heart rate signal and cardioversion synchronization signal in a manner well known in the prior art. The pressure transducer 118 may take the form of the pressure transducer illustrated and described in the Medtronic U.S. Pat. No. 4,485,813, also incorporated herein by reference in its entirety.

The occluding member 116 is depicted in FIG. 2 as a solid somewhat spherically shaped protrusion extending outwardly about the outer surface of the insulating sheath 114 and is provided to occlude the coronary vein until the lead fibroses in. It will be understood that the occluding member 116 may not be necessary inasmuch as the overall size of the lead body extending distally from the occluding member 116 may well fill and stretch the lumen of the selected coronary vein. In either case, if the vein is fibrosed or otherwise stretched tightly over the pressure transducer 118, the pressure transducer 118 will detect pressure proportional to the left ventricular pressure wave or pulse due to the location of the thebesian veins extending into the left ventricle accessible through the coronary sinus.

A commonly assigned U.S. Pat. No. 4,932,407 issued to Williams (incorporated herein by reference in its entirety) depicts a lead similar to that shown in FIG. 2, except that it does not include the occluding member 116 and pressure sensor 118. The lead disclosed in the Williams patent is also intended to be introduced into the coronary sinus to situate the cardioversion electrode 112 deep within the great cardiac vein to provide one cardioversion electrode in a system comprising one or two further electrodes spaced in or about the heart.

Figure 3:
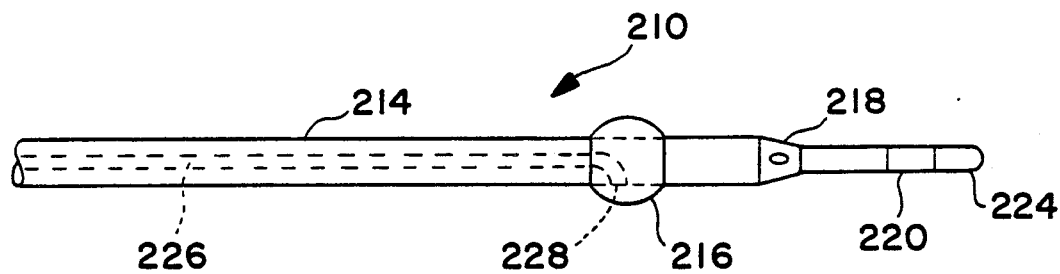
FIG. 3 is a partial plan view of a second embodiment of a pressure transducer bearing coronary sinus pacing and/or cardioversion lead of the present invention.

Turning now to FIG. 3, the second preferred embodiment of the pressure transducer bearing coronary sinus lead of the present invention is illustrated. In FIG. 3, the distal portion 210 does not include a cardioversion electrode section, it depicts only a unipolar pace sense electrode 220 and illustrates an inflatable occluding member 216 rather than the solid occluding member 116 of FIG. 2. The embodiment depicted in FIG. 3 thus presents an alternative design for the lead although it will be understood that features from both the FIG. 2 and FIG. 3 embodiments may be combined or eliminated in practice of the present invention.

In FIG. 3, the inflatable occluding member 216 is accessed from the proximal end of the lead (not shown) by the lumen 226 extending from the proximal end of the lead to an access port 228 inside the balloon occluding member 216. In practice, it would be contemplated that the lead depicted in FIG. 2 would be transvenously advanced into the coronary sinus and from the coronary sinus into a coronary vein until adequate pressure signals representative of the pressure of the left ventricular chamber are detected, whereupon the balloon member may be partially or completely inflated by saline solution.

The leads illustrated in FIGS. 2 and 3 show two forms of leads useful for practicing the present invention. However, it is envisioned that other types of leads bearing pressure sensors may also be useful in the context of the present invention. As noted above, pacing and/or sensing electrodes may be located in a more proximal position, or may be dispensed with entirely. Depending upon the diameter of the lead body, an occluding section, 116, 216, may be dispensed with entirely, or it may take a different form. Similarly, the particular pressure sensor illustrated may be replaced with other types of pressure sensors, and still remain within the scope of the invention. As such, the leads illustrated in FIGS. 2 and 3 should be considered exemplary, rather than limiting with regard to the scope of the invention.

Figure 4B:
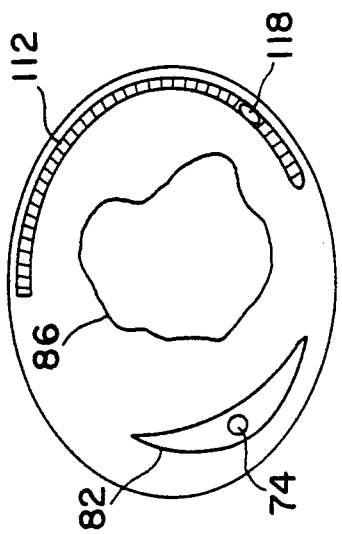
FIGS. 4A–4B are simplified drawings of a cutaway anterior view of the heart showing the arrangement of the pulse generator and leads comprising the system that performs the technique of the present invention wherein the pacing and/or cardioversion leads of the present invention are situated within the coronary sinus.
Figure 4A:
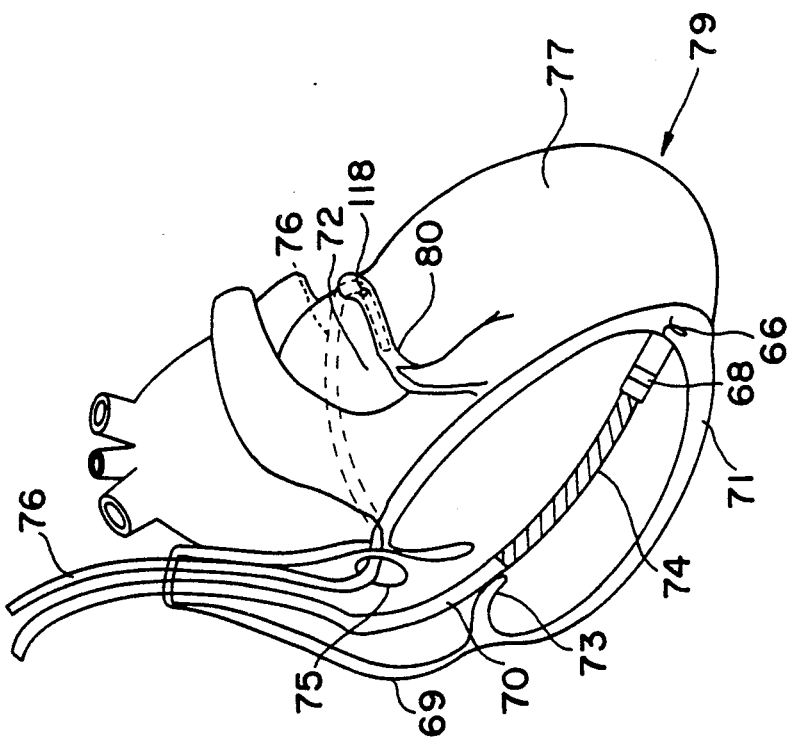

Turning now to FIGS. 4A-4B, the preferred embodiments of the present invention may be embodied in a system incorporating dual chamber pacing and/or cardioversion comprising a pulse generator and the leads of FIGS. 2 or 3 or variations of those leads, as well as further leads and stimulating electrodes arranged about the heart. FIGS. 4A-4B illustrate but one possible electrode combination to be employed with the pressure transducer bearing coronary sinus leads of the present invention.

FIG. 4A shows a cutaway view of the human heart in which the electrode leads have been mounted in their expected positions of use to provide a completely endocardial, transvenous defibrillation lead system. Ventricular lead 70 may take the form of the lead illustrated in FIG. 1 of the aforementioned Williams patent. Alternatively, it may be a defibrillation lead of the type employing one or more cylindrical electrodes adjacent its distal end, as illustrated in U.S. Pat. No. 4,355,646, issued to Kallok et al. This patent is also incorporated herein by reference in its entirety. In this view, it can be seen that the ventricular lead 70 passes through the atrium 69, and is secured in the apex of the right ventricle 71. Defibrillation lead 70 includes at least one elongated electrode surface 74 and located within the right ventricle 71 and a bipolar electrode pair for ventricular pacing and sensing comprising a helical electrode 66 and a ring electrode 68.

The pressure sensor bearing coronary sinus lead 76 is shown passing through the superior vena cava, into the opening of the coronary sinus 75, through the great cardiac vein 80, and extending around the base of the left ventricle 77. When so mounted, the elongated defibrillation electrode 78 extends from a point adjacent the opening of the coronary sinus 75 and into the great cardiac vein 80. This provides a large surface area defibrillation electrode which is generally well spaced from the ventricular defibrillation electrode 74 and provides good current distribution in the area of the left ventricle 77. It is desirable to extend the electrode 78 around the heart as far as possible. However, it is important not to extend the electrode 78 downward through the great vein 80 toward the apex 79 of the heart, as this will bring the coronary sinus and right ventricular electrodes into close proximity to one another, interfering with proper current distribution. Generally, the distal end of the electrode 78 should be roughly adjacent the left atrial appendage.

The pressure sensor 118 is shown in FIG. 3A located within the coronary vein 80 adjacent to the left ventricle. In this position, pressure proportional to the systolic and diastolic pressure of the left ventricle may be sensed.

In the electrode system illustrated in FIGS. 4A and 4B, the optional pacing and/or sensing electrodes 120, 124 are dispensed with in view of the inclusion of ventricular pacing electrodes 66 and 68 on lead 70. In the event that dual chamber pacing is desired, a set of atrial pacing and/or sensing electrodes should be provided. These may, for example, take the form of a pair of ring electrodes or a single ring electrode located on the body of the coronary sinus lead 76, adjacent to the opening of the coronary sinus into the right atrium. Sensing electrodes appropriate for this application are disclosed in the lead illustrated in FIG. 2 of the above-cited Williams patent. Alternatively, atrial pacing and/or sensing electrodes may be separately provided, in the form of either a unipolar or bipolar cardiac pacing lead, of any of the numerous types known to the art.

FIG. 4B shows a stylized cross-section of the heart, intended to illustrate the relative locations of the ventricular and coronary sinus electrodes. In this view, it can be seen that the right ventricular electrode 74 (visible in cross-section) is located within the right ventricular cavity 82, while the coronary sinus electrode 78 encircles the left ventricular cavity 86. In this view, it can be seen that a substantial percentage of the tissue of the left ventricle is located between electrode 74 and electrode 78, and that the pressure sensor 118 is located adjacent to the left ventricular cavity 86.

Figure 5:
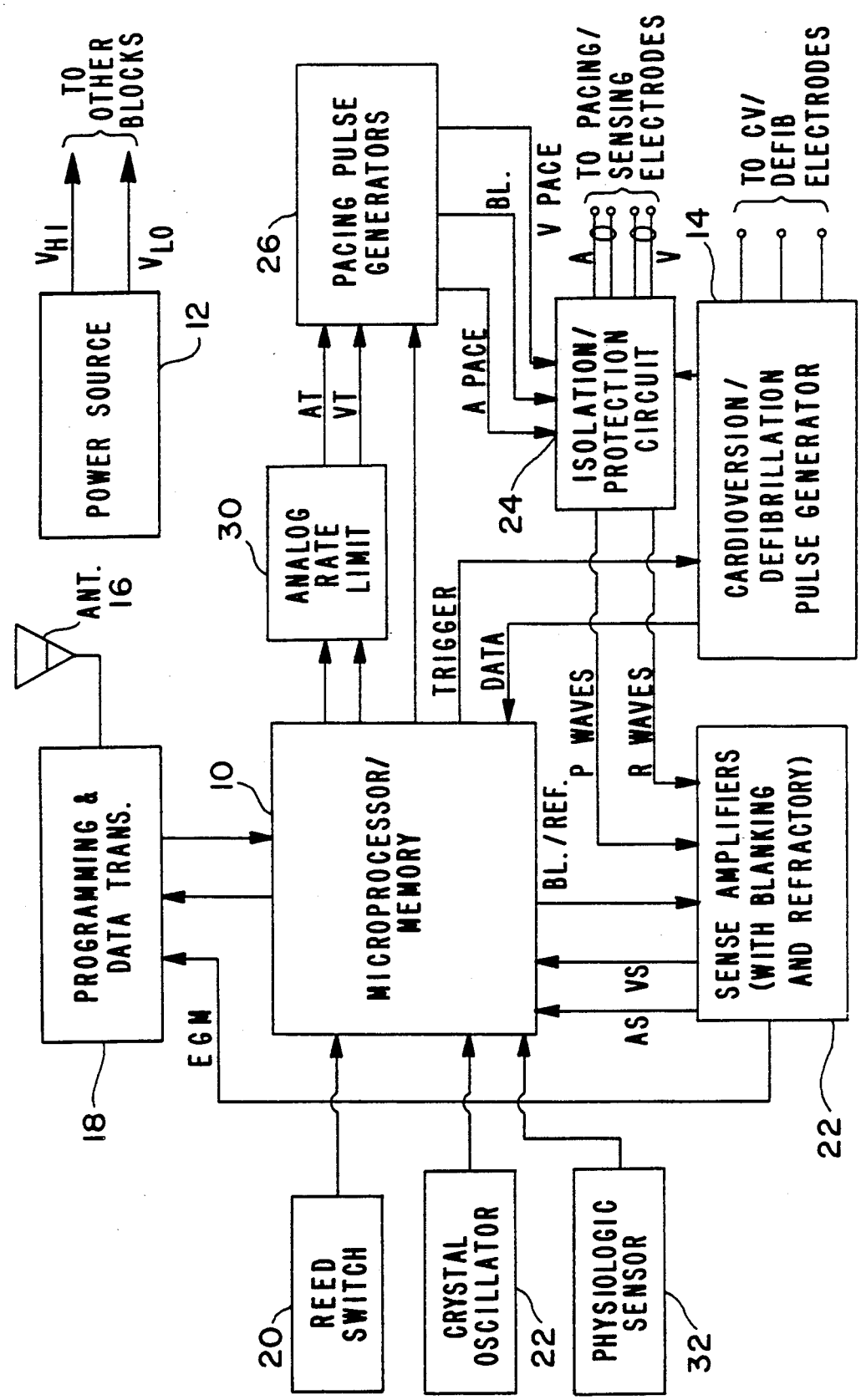
FIG. 5 is a block diagram of one form of pulse generator which may be adapted to be used in a system embodying the present invention.

Turning now to FIG. 5, a block diagram of the major components of an automatic implantable device for detecting and treating brady and tachyarrhythmias is depicted. It is contemplated that such a device would be implemented in analog and digital microcircuits under the control of a central microprocessor/memory block 10 powered by high (for cardioversion and defibrillation) and low (for the remaining circuitry on pacing therapies) power sources in block 12. The high power pulse generator block 14 would include the cardioversion and defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art.

It is contemplated that the implantable device depicted in FIG. 5 would function under the control of a resident operating program or software retained in memory within the microprocessor/memory block 10 and would be programmable by an external programmer/receiver (not illustrated in FIG. 5) communicating with the implanted device by radio frequency energy received or transmitted by antenna 16 under the control of the programming and data transmission block 18 and reed switch 20 which is responsive to an external magnet. The programming and data transmitting block 18 would be capable of receiving programming instructions and directing them to the memory within microprocessor/memory block 10 as well as transmitting data stored within the memory block 10 as well as an electrogram representing the patient's atrial and ventricular activity in a manner well known in the pacing art.

The timing of all processing functions, including the determination of atrial and ventricular cycle lengths, is controlled by system clocks within microprocessor/memory 10 driven by crystal oscillator 22 in a manner well known in the prior art of implantable digital pacemakers. The remaining blocks of FIG. 4 include the isolation/protection or interface block 24 which operates to direct ventricular, and optionally atrial pacing stimuli from the pacing pulse generator block 26 to respective ventricular and atrial output terminals which in turn are coupled through pacing leads to bipolar pacing electrodes situated in or near the ventricle, and optionally the atrium of the heart, respectively. In addition, the interface 24 (when unblanked) couples the atrial and ventricular electrograms (or P-waves and R-waves respectively) to the sense amplifier block 28. Interface 24 is blanked or prevented from passing any signals picked up on the bipolar atrial and ventricular pacing/sensing electrodes to the sense amplifier block 28 during short blanking intervals following the delivery of an atrial or ventricular pacing stimulus in a fashion well known in the pacing art.

Furthermore, the interface 24 disconnects or shorts out the pacing/sensing electrodes during the delivery and for a short period after the delivery of a cardioversion/defibrillation shock by application of a control signal to the interface 24 by the cardioversion/defibrillation pulse generator block 14.

The P-waves and R-waves transmitted through the interface 24 to the sense amplifiers 28 are amplified and shaped to generate atrial and ventricular signals AS and VS, respectively, which are conducted to microprocessor/memory 10 in order to derive the atrial and ventricular cycle lengths, the AV delay interval, and other intervals which may be appropriate to the overall function of the device. A further signal from the pressure sensor 118, 218 representative of left chamber blood pressure is also applied to the microprocessor/memory 10 in order to control the bradyarrhythmia pacing rate in DDDR, VVIR or other rate responsive mode of operation and to augment detection of tachyarrhythmias.

The microprocessor/memory 10 responds to atrial and ventricular AS and VS signals by generating appropriate atrial and ventricular refractory and blanking intervals which are in turn applied to the sense amplifier block 28 during certain windows of time following each respective AS and VS signal in a fashion well known in the pacing art.

It is contemplated that the system depicted in FIG. 4 may be programmed to operate in any of the known bradycardia single or dual chamber pacing modes. The signal from the physiologic sensor 32 may be employed to modify the atrial and ventricular escape intervals to allow for a certain range of atrial and ventricular pacing depending upon the level of the patient's activity in a fashion well known in the bradycardia pacing art. Suffice it to say, that atrial and ventricular escape intervals established in memory are compared against the atrial and ventricular cycle lengths encountered in the patient and, if a bradycardia condition exists, the microprocessor/memory 10 applies atrial and ventricular pace trigger signals AT and VT through analog rate limiter block 30 to the pacing pulse generator 26 which responds by developing he respective A pace and V pace signals. Analog rate limiter 30 operates telemetry atrial and ventricular pacing rates to a safe high rate into effect an appropriate upper rate behavior in the event that the spontaneous atrial rate exceeds the programmed upper rate limit in a fashion well known in the pacing art.

It is moreover contemplated that the microprocessor memory block 10 may be programmed to provide a regimen of successive treatment therapies to treat any tachyarrhythmia that is not corrected to sinus rhythm by the delivery of the first therapy in the regimen. The successive therapies may be programmed to be more aggressive and may include both pacing energy and cardioversion defibrillation shock therapies.

The system as described is rendered operational by resident software within the microprocessor/memory block 10 which is capable of distinguishing normal sinus rhythm within the acceptable upper and lower rate limits of the main brady pacing routine and distinguishing various types of tachyarrhythmias in accordance with algorithms known in the art.

The signals derived from the pressure sensors 118 or 218 and applied to the microprocessor/memory 10 of FIG. 4 may be employed to develop pulse, systolic and diastolic pressure values, long term mean or average values of these pressure values or both, short term mean or average values of the same pressures, the time derivatives (dP/dt) of the pressure signals and corresponding mean or average values thereof over short and long terms and the gross rate of change (ΔP/Δt) of same as all is described in the prior art referenced above. The microprocessor/memory 10 may include specific circuits for differentiating the pressure signal, measuring the peak pulse, systolic and diastolic pressures and the mean and gross rate of change of these values. For example, the calculation of the mean blood pressure may be carried out in various manners. For instance, the microprocessor/memory 10 may consist of a mean value rectifying circuit having a suitable time constant including two peak detecting amplifiers which are connected to the signal from the pressure transducer with opposite polarities so that the one amplifier produces an output signal representing the systolic blood pressure, whereas the other amplifier produces an output signal representing the diastolic blood pressure. These two output signals are supplied to an analog summing circuit which sums the signals according to the equation:

$$P_{mean} = P_{diastolic} + 1/\sqrt{-2}(P_{systolic} - P_{diastolic}).$$

This is approximate an expression for the mean blood pressure $P_{mean}$ based upon a substitution of a triangular curve for the pulse wave. These pressure values may be employed in any of the algorithms described in the aforementioned prior art to develop a pacing rate control system or to detect or confirm the detection of a hemodynamically compromising tachyarrhythmia. Thus, the algorithms disclosed in the aforementioned U.S. Pat. Nos. 4,566,456, 4,774,950, 4,899,751 and the Olson et al abstract are incorporated herein by reference.

The ability of the system in FIG. 4 to distinguish high rates which result in hemodynamic compromise, from high ventricular rates accompanied by normal hemodynamic operation or only moderate hemodynamic compromise can be used to select the aggressiveness of the cardioversion therapy to be applied. For example, in the presence of high ventricular rate, within a predetermined range believed to be generally indicative of ventricular tachycardia, and in the presence of normal, or only somewhat compromised hemodynamic functions, the first anti-tachyarrhythmia therapy attempted may be an anti-tachyarrhythmia pacing therapy such as burst pacing, decremental overdrive pacing, or multiple pulse pacing methods, of any of the types known to the art. The degree to which hemodynamic function has been compromised is a useful indicator of how rapidly cardioversion must be effected, and with greater hemodynamic compromise, a greater degree of aggressiveness for the initial anti-tachyarrhythmia therapy provided is desirable. Similarly, the entire sequence of therapies to be employed may be specified based on the degree of hemodynamic compromise detected by the pressure sensor, with a more rapid increase in the aggressiveness of the sequential therapies specified in response to detection of greater hemodynamic compromise. The therapy sequence may be specified after a single measurement made prior to the first therapy or may be updated by later pressure measurements taken after initiation of antitachyarrhythmia therapy.

The present invention provides a significant advancement in the treatment of patients having malfunctioning hearts through the detection of left heart chamber pressure values without invading the myocardium or the left heart chambers or high pressure vessels. The systems of the present invention operate automatically to process the left heart related pressure values to develop pacing rate control and cardioversion detection signals effective to distinguish normal heart function from abnormal heart function in a variety of situations. Although not expressly illustrated, hereinbefore it will be understood that the principles of the present invention may be applied as well to the detection and treatment of congestive heart failure by either electrical stimulation or dispensing of drugs. In this regard, it will be understood that the pressure transducer bearing coronary sinus lead of the present invention may be employed with an implantable drug dispenser of the type described in Ellinwood U.S. Pat. No. 4,003,379 to control the delivery of electrical stimulation and/or drugs in the treatment of congestive heart failure.

It is to be understood that the foregoing detailed description and accompanying illustrations have been set out by way of example, not by way of limitation. Numerous other embodiments and variants are possible, without departing from the spirit and scope of the invention defined in the appended claims.

What is claimed is:

1. A method for controlling cardiac tachyarrhythmias by passing an electrical current through the heart which comprises:
   disposing at least first and second electrodes in relation to the heart;
   disposing a pressure transducer within the coronary sinus region of the heart adjacent to the left heart chambers;
   detecting a signal proportional to the left heart chamber blood pressure by said pressure transducer and providing a first signal in response to detection of normal heart pumping and a second signal in response to detection of abnormal heart pumping, characteristic of hemodynamic insufficiency; and
   supplying cardioversion energy to said heart in response to said second signal by application of stimulating pulses across said electrodes.

2. The method of claim 1 wherein said step of disposing at least first and second electrodes further comprises the step of providing at least one of said electrodes in said coronary sinus region in specific relation with said pressure transducer.

3. The method of claims 1 or 2 wherein said detecting step includes detecting a pressure proportional to left ventricular systolic blood pressure.

4. The method of claims 1 or 2 wherein said detecting step includes detecting a pressure proportional to left ventricular pulse pressure.

5. The method of claims 1 or 2 wherein said detecting step includes detecting a signal proportional to left ventricular peak to peak blood pressure.

6. The method of claims 1 or 2 wherein said detecting step includes detecting differentiated time rate of change (dP/dt) pressure values.

7. The method of claims 1 or 2 wherein said detecting step includes detecting time rate of change ($\Delta P/\Delta t$) pressure values.

8. The method of claim 1 wherein said step of disposing a pressure transducer in the coronary sinus or coronary vein region further comprises:
   providing a pressure transducer in the distal portion of a lead body adapted to be inserted into the coronary sinus and from the coronary sinus into a coronary vein; and
   transvenously advancing said distal portion of said lead body through the superior vena cava, the right atrium, the coronary sinus, and into said coronary vein.

9. The method of claim 8 further comprising the step of:
   occluding the coronary vein proximal to the location of the pressure transducer when said pressure transducer is situated in the coronary vein.

10. The method of claim 9 wherein said step of occluding the coronary vein further comprises the step of:
    providing an occluding member on said lead proximal to said pressure transducer.

11. Apparatus for controlling cardiac tachyarrhythmias by passing an electrical current through the heart which comprises:
    means for disposing at least first and second electrodes in relation to the heart;
    means for disposing a pressure transducer within the coronary sinus or coronary vein of the heart adjacent to the left heart chambers;
    means for detecting a pressure proportional to left heart chamber blood pressure by said pressure transducer and providing a first signal in response to normal heart pumping and a second signal in response to abnormal heart pumping characteristic of hemodynamic insufficiency; and
    means for supplying cardioverting energy to said heart in response to said second signal by application of stimulating pulses by means of said first and second electrodes.

12. The apparatus of claim 11 wherein said means for disposing at least first and second electrodes further comprises means for providing at least one of said electrodes in said coronary sinus region in specific relation with said pressure transducer.

13. The method of claims 11 or 12 wherein said means for detecting pressure includes means for detecting pressure proportional to left ventricular systolic blood pressure.

14. The method of claims 11 or 12 wherein said means for detecting pressure includes means for detecting pressure proportional to left ventricular pulse pressure.

15. The method of claims 11 or 12 wherein said means for detecting pressure includes means for detecting pressure proportional to left ventricular peak to peak blood pressure.

16. The method of claims 11 or 12 wherein said means for detecting pressure includes means for detecting differentiated time rate of change (dP/dt) pressure values.

17. The method of claims 11 or 12 wherein said means for detecting pressure includes means for detecting gross time rate of change ($\Delta P/\Delta t$) pressure values.

18. The apparatus of claim 11 wherein said means for disposing a pressure transducer in the coronary sinus or coronary vein region further comprises:
    means for providing a pressure transducer in the distal portion of a lead body adapted to be inserted into the coronary sinus and from the coronary sinus into a coronary vein.

19. The apparatus of claim 18 further comprising:
    means for occluding said coronary vein proximal to the location of the pressure transducer when said pressure transducer is situated in said coronary vein.

20. The apparatus of claim 19 wherein said means for occluding the coronary vein further comprises:
    means for providing an occluding member on said lead proximal to said pressure transducer.

21. A method for regulating cardiac pacing rate in response to a patient's left heart blood pressure which comprises:
    disposing at least first and second electrodes in relation to the heart;
    disposing a pressure transducer within the coronary sinus region of the heart adjacent to the left heart chambers;
    detecting pressure signals by said pressure transducer;
    providing a pacing rate control signal derived from said pressure signals; and
    supplying pacing energy stimulation pulses to said electrodes at a rate established by said rate control signal.

22. The method of claim 21 wherein said step of disposing at least first and second electrodes further comprises the step of providing at least one of said electrodes in said coronary sinus region in specific relation with said pressure transducer.

23. The method of claim 21 wherein said step of disposing a pressure transducer in the coronary sinus region further comprises:
    providing a pressure transducer in the distal portion of a lead body adapted to be inserted into the coronary sinus and from the coronary sinus into a coronary vein; and
    transvenously advancing a distal portion of said lead body through the superior vena cava, the right atrium, the coronary sinus, and into a coronary vein.

24. The method of claim 21 or 23 wherein said step of detecting pressure signals includes detecting pressure signals proportional to left ventricular systolic block pressure.

25. The method of claims 21 or 23 wherein said step of detecting pressure signals includes detecting pressure signals proportional to left ventricular pulse pressure.

26. The method of claims 21 or 23 wherein said step of detecting pressure signals includes detecting left pressure signals proportional to ventricular peak to peak blood pressure.

27. The method of claims 21 or 23 wherein said step of detecting pressure signals includes detecting differentiated time rate of change (dP/dt) pressure values.

28. The method of claims 21 or 23 wherein said step of detecting pressure signals includes detecting time rate of change (ΔP/Δt) pressure values.

29. The method of claim 21 further comprising the step of:
   occluding said coronary vein proximal to the location of said pressure transducer when said pressure transducer is situated in said coronary vein.

30. The method of claim 29 wherein said step of occluding said coronary vein further comprises the step of:
   providing an occluding member on said lead proximal to said pressure transducer.

31. Apparatus for regulating cardiac pacing rate in response to a patient's left heart blood pressure which comprises:
   means for disposing at least first and second electrodes in relation to the heart;
   means for disposing a pressure transducer within the coronary sinus region of the heart adjacent to the left heart chambers;
   means for detecting pressure signals by said pressure transducer and providing a pacing rate control signal derived from the pressure signal; and
   means for supplying pacing energy stimulation pulses to said electrodes at a rate established by said rate control signal.

32. The apparatus of claim 31 wherein said means for disposing at least first and second electrodes further comprises means for providing at least one of said electrodes in said coronary sinus region in specific relation with said pressure transducer.

33. The apparatus of claim 32 wherein the means for disposing a pressure transducer in the coronary sinus region further comprises:
   means for providing a pressure transducer in the distal portion of a lead body adapted to be inserted into the coronary sinus and from the coronary sinus into a coronary vein.

34. The apparatus of claims 31 or 33 wherein said means for detecting pressure signals includes means for detecting signals proportional to left ventricular systolic blood pressure.

35. The apparatus of claims 31 or 33 wherein said means for detecting pressure signals includes means for detecting signals proportional to left ventricular pulse pressure.

36. The apparatus of claims 31 or 33 wherein said means for detecting pressure signals includes means for detecting signals proportional to left ventricular peak to peak blood pressure.

37. The apparatus of claims 31 or 33 wherein said means for detecting pressure signals includes means for detecting differentiated time rate of change (dP/dt) pressure values.

38. The apparatus of claims 31 or 33 wherein said means for detecting pressure signals includes means for detecting gross time rate of change (ΔP/Δt) pressure values.

39. The apparatus of claim 31 further comprising:
   means for occluding said coronary vein proximal to location of said pressure transducer when said pressure transducer is situated in said coronary vein.

40. The apparatus of claim 39 wherein said means for occluding said coronary vein further comprises:
   means for providing an occluding member on said lead proximal to the pressure transducer.

* * * * *